United States Patent
Root et al.

(10) Patent No.: US 8,292,850 B2
(45) Date of Patent: Oct. 23, 2012

(54) COAXIAL GUIDE CATHETER FOR INTERVENTIONAL CARDIOLOGY PROCEDURES

(75) Inventors: Howard Root, Excelsior, MN (US); Gregg Sutton, Maple Grove, MN (US); Jeffrey M Welch, Maple Grove, MN (US); Jason M Garrity, Minneapolis, MN (US)

(73) Assignee: Vascular Solutions, Inc., Minneapolis, MN (US)

(*) Notice: Subject to any disclaimer, the term of this patent is extended or adjusted under 35 U.S.C. 154(b) by 0 days.

(21) Appl. No.: 13/359,059

(22) Filed: Jan. 26, 2012

(65) Prior Publication Data
US 2012/0165756 A1 Jun. 28, 2012

Related U.S. Application Data

(62) Division of application No. 12/824,734, filed on Jun. 28, 2010, now Pat. No. 8,142,413, which is a division of application No. 11/416,629, filed on May 3, 2006, now Pat. No. 8,048,032.

(51) Int. Cl.
*A61M 5/178* (2006.01)
*A61M 25/00* (2006.01)

(52) U.S. Cl. .................... 604/164.01; 604/525

(58) Field of Classification Search ............ 604/103.04, 604/103.09, 160–162, 164.01, 164.02, 164.09–164.11, 604/525
See application file for complete search history.

(56) References Cited

U.S. PATENT DOCUMENTS

| | | | |
|---|---|---|---|
| 4,813,930 A | 3/1989 | Elliott | |
| 4,832,028 A | 5/1989 | Patel | |
| 4,932,413 A | 6/1990 | Shockey et al. | |
| 5,098,412 A | 3/1992 | Shiu | |
| 5,122,125 A | 6/1992 | Deuss | |
| 5,472,425 A | 12/1995 | Teirstein | |
| 5,658,263 A | 8/1997 | Dang et al. | |
| 5,776,141 A | 7/1998 | Klein et al. | |
| 6,159,195 A | 12/2000 | Ha et al. | |
| 6,338,725 B1 | 1/2002 | Hermann et al. | |
| 6,475,195 B1 | 11/2002 | Voda | |
| 6,595,952 B2 | 7/2003 | Forsberg | |
| 6,610,068 B1 | 8/2003 | Yang | |
| 6,638,268 B2 | 10/2003 | Niazi | |
| 6,689,144 B2 | 2/2004 | Gerberding | |
| 6,706,018 B2 | 3/2004 | Westlund et al. | |
| 6,755,812 B2 | 6/2004 | Peterson et al. | |

(Continued)

OTHER PUBLICATIONS

Saeko Takahashi et al.; New Method to Increase a Backup Support of a 6 French Guiding Coronary Catheter; Catheterization and Cardiovascular Interventions 63:452-456 (2004), 5 pages; Published online in Wiley InterScience (www.interscience.wiley.com).

(Continued)

*Primary Examiner* — Kevin C Sirmons
*Assistant Examiner* — Bradley Osinski
(74) *Attorney, Agent, or Firm* — Patterson Thuente Christensen Pedersen, P.A.

(57) ABSTRACT

A coaxial guide catheter to be passed through guide catheter having a first lumen, for use with interventional cardiology devices that are insertable into a branch artery that branches off from a main artery. The coaxial guide catheter is extended through the lumen of the guide catheter and beyond the distal end of the guide catheter and inserted into the branch artery. The device assists in resisting axial and shear forces exerted by an interventional cardiology device passed through the second lumen and beyond the flexible distal tip portion that would otherwise tend to dislodge the guide catheter from the branch artery.

24 Claims, 13 Drawing Sheets

U.S. PATENT DOCUMENTS

| | | |
|---|---|---|
| 6,860,876 B2 | 3/2005 | Chen |
| 7,697,996 B2 | 4/2010 | Manning et al. |
| 7,717,899 B2 | 5/2010 | Bowe et al. |
| 2003/0195546 A1 | 10/2003 | Solar et al. |
| 2004/0127927 A1 | 7/2004 | Adams |
| 2005/0004523 A1 | 1/2005 | Osborne et al. |
| 2005/0182437 A1 | 8/2005 | Bonnette et al. |
| 2007/0260219 A1 | 11/2007 | Root et al. |

OTHER PUBLICATIONS

U.S. Appl. No. 11/416,629, filed Jun. 28, 2010; Howard Root et al.
U.S. Appl. No. 12/824,734, filed Jun. 28, 2010, Howard Root et al.

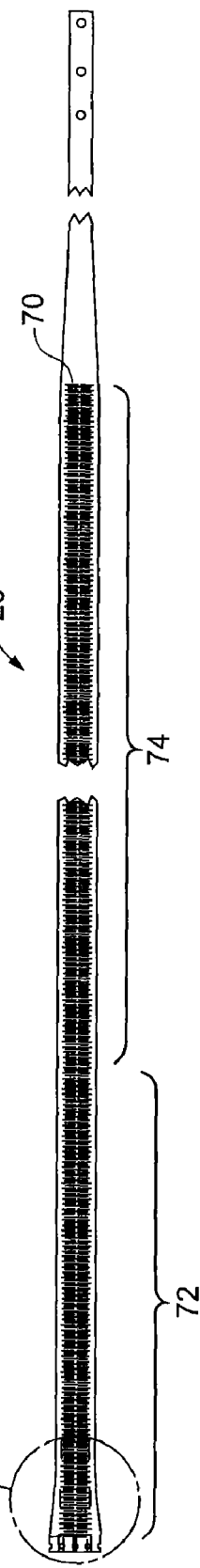
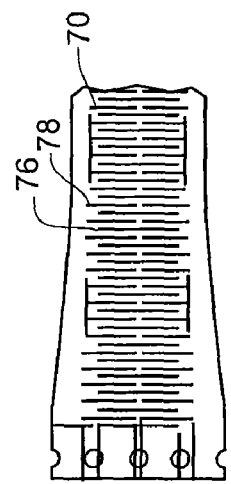
Fig. 10
Fig. 11

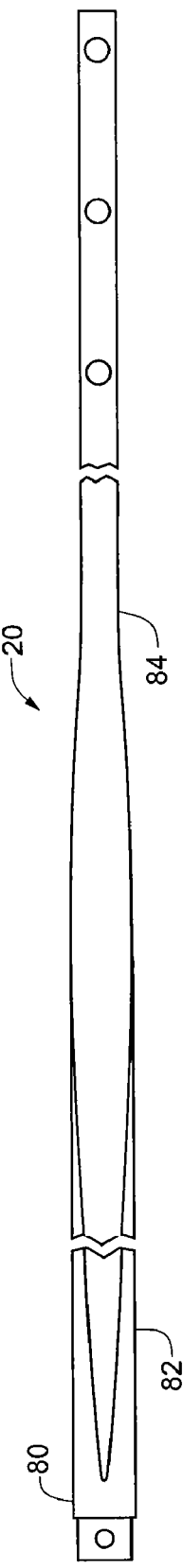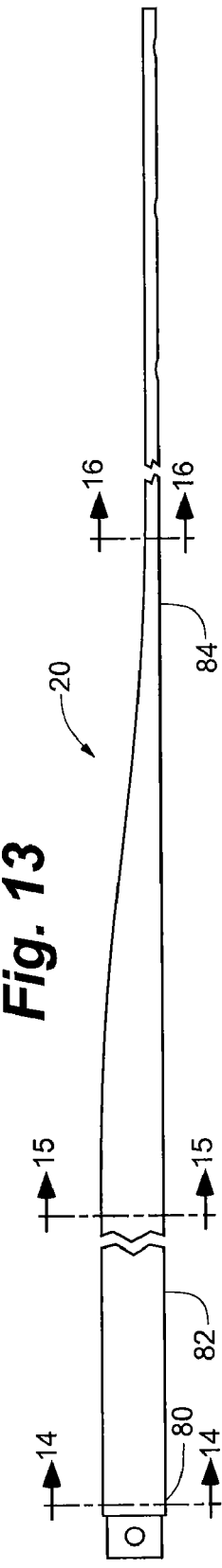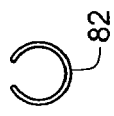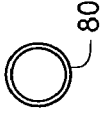

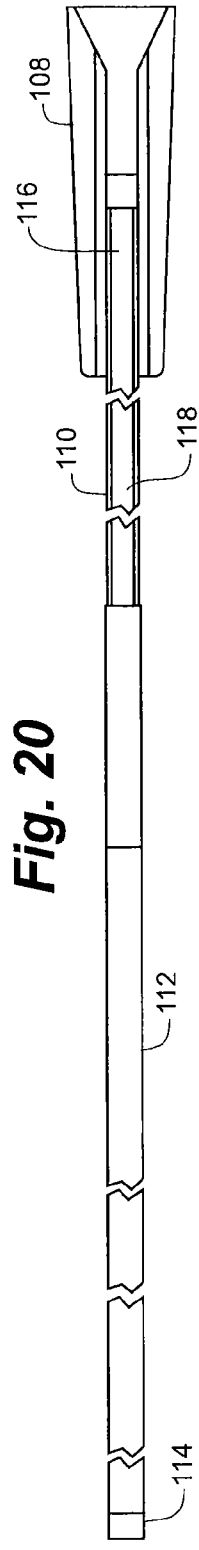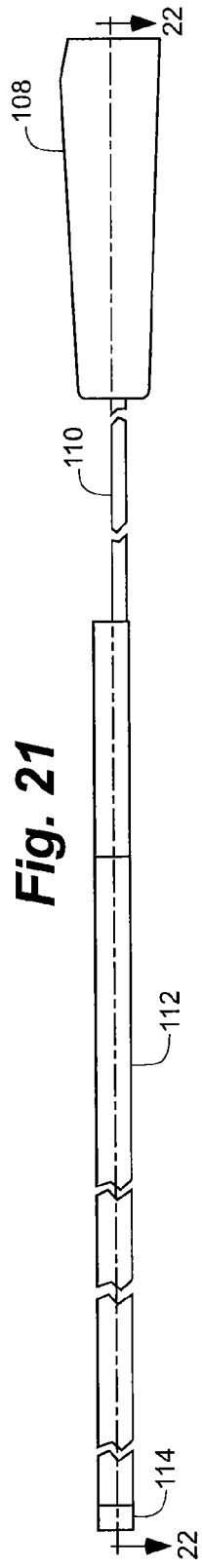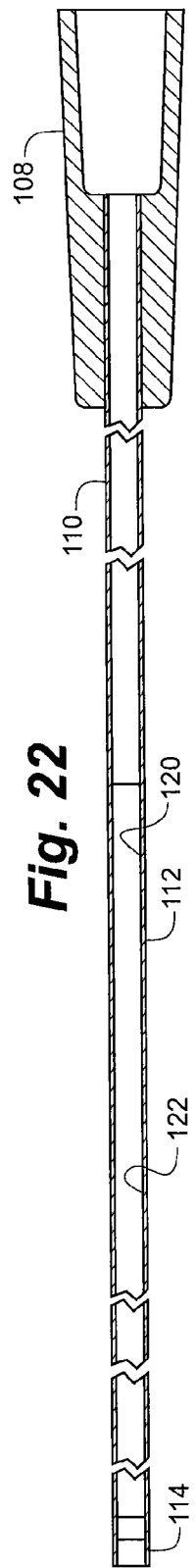

COAXIAL GUIDE CATHETER FOR INTERVENTIONAL CARDIOLOGY PROCEDURES

RELATED APPLICATIONS

This application is a divisional of application Ser. No. 12/824,734, filed Jun. 28, 2010 now U.S. Pat. No. 8,142,413 entitled "Coaxial Guide Catheter for Interventional Cardiology Procedures", which is divisional of application Ser. No. 11/416,629, filed May 3, 2006 now U.S. Pat. No. 8,048,032 entitled "Coaxial Guide Catheter for Interventional Cardiology Procedures".

FIELD OF THE INVENTION

The present invention relates generally to catheters used in interventional cardiology procedures. More particularly the present invention relates to methods and apparatus for increasing backup support for catheters inserted into the coronary arteries from the aorta.

BACKGROUND OF THE INVENTION

Interventional cardiology procedures often include inserting guidewires or other instruments through catheters into coronary arteries that branch off from the aorta. For the purposes of this application, the term "interventional cardiology devices" is to be understood to include but not be limited to guidewires, balloon catheters, stents and stent catheters. In coronary artery disease the coronary arteries may be narrowed or occluded by atherosclerotic plaques or other lesions. These lesions may totally obstruct the lumen of the artery or may dramatically narrow the lumen of the artery. Narrowing is referred to as stenosis. In order to diagnose and treat obstructive coronary artery disease it is commonly necessary to pass a guidewire or other instruments through and beyond the occlusion or stenosis of the coronary artery.

In treating a stenosis, a guide catheter is inserted through the aorta and into the ostium of the coronary artery. This is sometimes accomplished with the aid of a guidewire. A guide catheter is typically seated into the opening or ostium of the artery to be treated and a guidewire or other instrument is passed through the lumen of the guide catheter and inserted into the artery beyond the occlusion or stenosis. Crossing tough lesions can create enough backward force to dislodge the guide catheter from the ostium of the artery being treated. This can make it difficult or impossible for the interventional cardiologist to treat certain forms of coronary artery disease.

Prior attempts to provide support to the guiding catheter to prevent backward dislodgement from the coronary ostium (referred to as "backup support") fall generally into four categories.

First are guiding catheters that, through a combination of shape and stiffness, are configured to draw backup support from engaging the wall of the aortic arch opposing the ostium of the coronary artery that is being accessed. Examples of this approach can be found in U.S. Pat. No. 6,475,195 issued to Voda and U.S. Pat. No. 5,658,263 issued to Dang et al. These guiding catheters all share the common limitation that a guide catheter stiff enough to provide adequate backup support is often too stiff to be safely inserted into the aorta without the possibility of causing damage to the aortic wall. In addition, attempts to deep seat the guide catheter have been made but the rigid nature of the guide catheter creates the risk that the guide catheter may damage the coronary artery wall or that the guide catheter may occlude the coronary artery and interfere with blood flow to the heart muscle.

Second are guiding catheters that include a retractable appendage. The appendage in these catheters can be extended to engage the opposing wall of the aortic arch to provide backup support or the appendage may be placed under tension to stiffen a bend in the catheter to provide backup support. Examples of this approach may be found in U.S. Pat. No. 4,813,930 issued to Elliot; U.S. Pat. No. 5,098,412 issued to Shiu; and U.S. Pat. No. 6,860,876 issued to Chen. These guiding catheters tend to be somewhat mechanically complex and have not been widely adopted by practitioners.

Third are guide catheters that have a portion that seeks to expand laterally to grip the interior wall of the ostium of the coronary artery to provide a force acting in opposition to the backward forces created when trying to maneuver a therapeutic device past a lesion or blockage in the coronary artery. These devices can include a balloon secured to a guidewire or a catheter or another device for expanding to grip the walls of the coronary artery from within. Examples of this approach may be found in U.S. Pat. No. 4,832,028 issued to Patel; U.S. Pat. No. 6,595,952 issued to Forsberg; and U.S. Published Application No. 2005/0182437 by Bonnette et al. Again, these devices tend to be mechanically complex and can completely occlude the coronary ostium thus stopping perfusion of the coronary artery.

A fourth technique includes the placement of a smaller guide catheter within a larger guide catheter in order to provide added support for the crossing of lesions or for the distal delivery of balloons and stents. This technique has been described in an article by Takahashi entitled "New Method to Increase a Backup Support of Six French Guiding Coronary Catheter," published in Catheterization and Cardiovascular Interventions, 63:452-456 (2004). This technique is used in order to provide a method of deep seating the guide catheter within the ostium of the coronary artery. Deep seating refers to inserting the catheter more deeply into the ostium of the coronary artery than typically has been done before. Unfortunately, deep seating by this technique with a commonly available guide catheter creates the risk that the relatively stiff, fixed curve, guide catheter will damage the coronary artery. This damage may lead to dissection of the coronary artery when the catheter is advanced past the ostium.

Several other problems arise when using a standard guide catheter in this catheter-in-a-catheter fashion. First, the inner catheters must be substantially longer than the one hundred centimeter guide catheter. Second, a new hemostasis valve must be placed on the inner guide catheter which prevents the larger guide catheter from being used for contrast injections or pressure measurements. Third, the smaller guide catheter still must be inserted into the coronary vessel with great care since the smaller guide catheter has no tapered transition or dilator at its tip and does not run over a standard 0.014 inch guidewire.

Thus, the interventional cardiology art would benefit from the availability of a system that would be deliverable through standard guide catheters for providing backup support by providing the ability to effectively create deep seating in the ostium of the coronary artery.

SUMMARY OF THE INVENTION

The present invention is a coaxial guide catheter that is deliverable through standard guide catheters by utilizing a guidewire rail segment to permit delivery without blocking use of the guide catheter. The coaxial guide catheter preferably includes a tapered inner catheter that runs over a standard 0.014 inch coronary guidewire to allow atraumatic placement within the coronary artery. This feature also allows removal of the tapered inner catheter after the coaxial guide catheter is in place. The tapered inner catheter provides a gradual transition from the standard 0.014 inch diameter guidewire to the diameter of the coaxial guide catheter which is typically five to eight French.

The coaxial guide catheter preferably can be delivered through commonly existing hemostatic valves used with guide catheters while still allowing injections through the existing Y adapter. In addition, the coaxial guide catheter preferably has an inner diameter that is appropriate for delivering standard coronary treatment devices after it is placed in the coronary artery.

In one embodiment, the coaxial guide catheter is made in at least three sizes corresponding to the internal capacity of 8 French, 7 French, and 6 French guide catheters that are commonly used in interventional cardiology procedures. An 8 French catheter has an internal diameter greater than or equal to 0.088 inches. A 7 French catheter has an internal diameter greater than or equal to 0.078 inches. A 6 French guide catheter has an internal diameter greater than or equal to 0.070 inches. Thus, for three exemplary sizes the effective internal diameter of the coaxial guide catheter may be as follows. For a 7 French in 8 French coaxial guide catheter, the internal diameter should be greater than or equal to 0.078 inches. For a 6 French in 7 French coaxial guide catheter the internal diameter should be greater than or equal to 0.070 inches. For a 5 French in 6 French coaxial guide catheter the internal diameter should be greater than or equal to 0.056 inches.

Interventional cardiology procedures are typically carried out under fluoroscopy or another x-ray or imaging technique. Therefore, one embodiment of the coaxial guide catheter of the present invention includes a radiopaque marker at its distal tip to facilitate positioning and manipulation of the coaxial guide catheter.

The present invention generally includes the coaxial guide catheter and a tapered inner catheter. The coaxial guide catheter includes a tip portion, a reinforced portion, and a substantially rigid portion. The coaxial guide catheter will generally have an overall length of preferably approximately 125 cm, though this should not be considered limiting.

In one embodiment, the tip portion may include a soft tip and a marker band. The soft tip is tapered and may be formed from a low durometer polymer or elastomer material such as polyether block amide polymer, (PEBA, Pebax®) the marker band may be formed from a platinum iridium alloy sandwiched between the Pebax® that extends from the bump tip and a PTFE liner.

In one embodiment, the reinforced portion may be reinforced, preferably with metallic fibers in a braided or coiled pattern. The braided or coiled portion is lined by a PTFE liner and may be covered on its exterior with Pebax®. The braided or coiled portion may extend approximately 20 to 110 cm in length. In one exemplary embodiment, the braided portion extends approximately 32 to 36 cm.

Preferably, the rigid portion may be advantageously formed from a stainless steel or Nitinol tube. The rigid portion may be joined to the braid or coil portion by welding. The rigid portion may include a cutout portion and a full circumference portion. For example, the cutout portion may include a section where about 45% of the circumference of the cylindrical tubular structure has been removed. The cutout portion may also include a section where 75-90% of the circumference of the tubular structure has been removed. In one exemplary embodiment, the portion having approximately 45% removed may extend for approximately 75 cm and the portion having 75-90% of the structure removed extends for about 15 cm.

The full circumference portion of the rigid portion is typically located at the most proximal end of the coaxial guide catheter.

The rigid portion may include a plurality of radially oriented slits or other cuts in its distal portion to increase and control the flexibility of the rigid portion In an exemplary embodiment, the tapered inner catheter generally includes a tapered inner catheter tip and a cutout portion. The tapered inner catheter tip includes a tapered portion and a straight portion. The tapered portion is typically at the most distal end of the tapered inner catheter. Both the straight portion and the tapered portion are pierced by a lumen through which a guidewire may be passed.

The cutout portion supports a track passing along the concave side thereof that continues from the lumen that passes through the straight portion and the tapered portion. The tapered inner catheter may also have a clip or snap attachment at its proximal end to releasably join the tapered inner catheter to the coaxial guide catheter.

In operation, the tapered inner catheter is inserted inside and through the coaxial guide catheter. The tapered inner catheter is positioned so that the tapered inner catheter tip extends beyond the tip portion of the coaxial guide catheter. The coaxial guide catheter-tapered inner catheter combination may then be inserted into a blood vessel that communicates with the aorta. The coaxial guide catheter-tapered inner catheter combination may be threaded over a preplaced 0.014 inch guidewire. The tapered inner catheter-coaxial guide catheter combination is advanced up the aorta until the tapered inner catheter is passed into the ostium of a coronary artery over the guidewire. Once the coaxial guide catheter-tapered inner catheter combination has been inserted sufficiently into the ostium of the coronary artery to achieve deep seating the tapered inner catheter may be removed. During this entire process at least part of the coaxial guide catheter-tapered inner catheter combination is located inside of the guide catheter.

Once the tapered inner catheter is removed a cardiac treatment device, such as a guidewire, balloon or stent, may be passed through the coaxial guide catheter within the guide catheter and into the coronary artery. As described below, the presence of the coaxial guide catheter provides additional backup support to make it less likely that the coaxial guide catheter guide catheter combination will be dislodged from the ostium of the coronary artery while directing the coronary therapeutic device past a tough lesion such as a stenosis or a chronic arterial occlusion.

A guide catheter inserted into the ostium of a branch artery where it branches off from a larger artery is subject to force vectors that tend to dislodge the distal end of the guide catheter from the ostium of the branch artery when a physician attempts to direct a guidewire or other interventional cardiology device past an occlusive or stenotic lesion in the branch artery. This discussion will refer to a guide wire but it is to be understood that similar principles apply to other interventional cardiology devices including balloon catheters and stent catheters.

One of the forces that act on the guide catheter is an axial force substantially along the axis of the branch artery and the portion of the guide catheter that is seated in the ostium. This force vector is a reactive force created by the pushing back of the guide wire against the guide catheter as the physician tries to force the guidewire through or past the lesion. It tends to push the distal end of the catheter out of the ostium in a direction parallel to the axis of the branch artery and the axis of the distal end of the guide catheter.

Another of the force vectors that acts on the guide catheter is a shearing force that tends to dislodge the distal end of the guide catheter from the ostium of the branch artery in a direction perpendicular to the axis of the branch artery and the axis of the distal end of the guide catheter. This force vector arises from curvature of the guide catheter near its distal end and the guide wire pushing on the curved portion of the guide catheter as the physician applies force to the guidewire. The coaxial guide catheter of the present invention assists in resisting both the axial forces and the shearing forces that tend to dislodge a guide catheter from the ostium of a branch artery.

The system is deliverable using standard techniques utilizing currently available equipment. The present invention also allows atraumatic placement within the coronary artery. Further, the invention is deliverable through an existing hemostatic valve arrangement on a guide catheter without preventing injections through existing Y adapters. Finally, the invention has an inner diameter acceptable for delivering standard coronary devices after it is placed in the blood vessel.

BRIEF DESCRIPTION OF THE DRAWINGS

FIG. 10 is a flat pattern for making relief cuts in a curved rigid portion of the coaxial guide catheter in accordance with the present invention;

FIG. 11 is a detailed view taken from FIG. 10;

FIG. 12 is a plan view of the rigid portion in accordance with the present invention;

FIG. 13 is an elevational view of the rigid portion;

FIG. 14 is a sectional view of the rigid portion taken along section line 14-14 of FIG. 13; and FIG. 15 is a sectional view of the rigid portion taken along section line 15-15 of FIG. 13.

FIG. 16 is a sectional view of the rigid portion taken along section line 16-16 of FIG. 13.

FIG. 20 is a plan view of a coaxial guide catheter in accordance with the present invention.

FIG. 21 is an elevational view of a coaxial guide catheter in accordance with the present invention.

FIG. 22 is a cross-sectional view taken along section line 22-22 of FIG. 21.

DETAILED DESCRIPTION OF THE DRAWINGS

Figure 1:
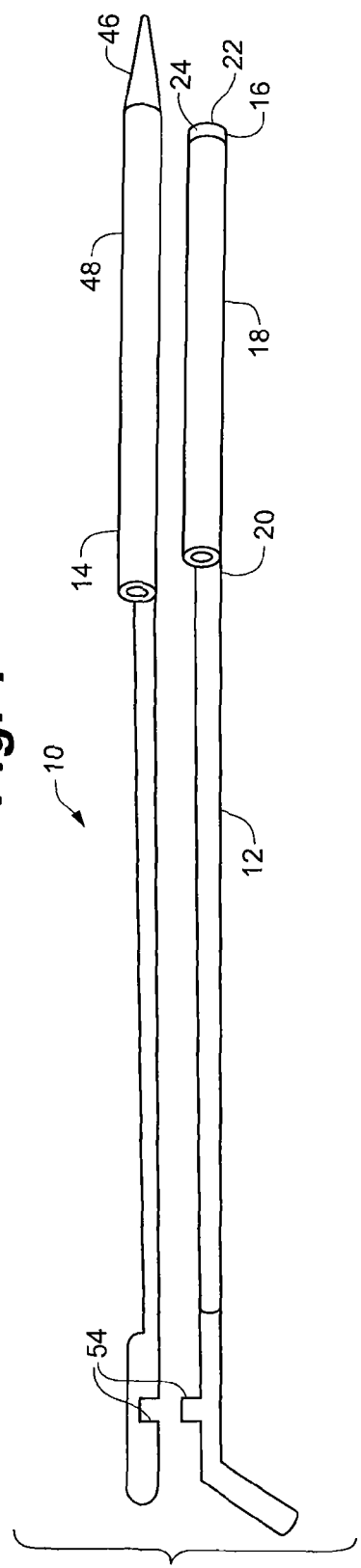
FIG. 1 is a schematic depiction of the coaxial guide catheter and a tapered inner catheter in accordance with the present invention.
Figure 2:
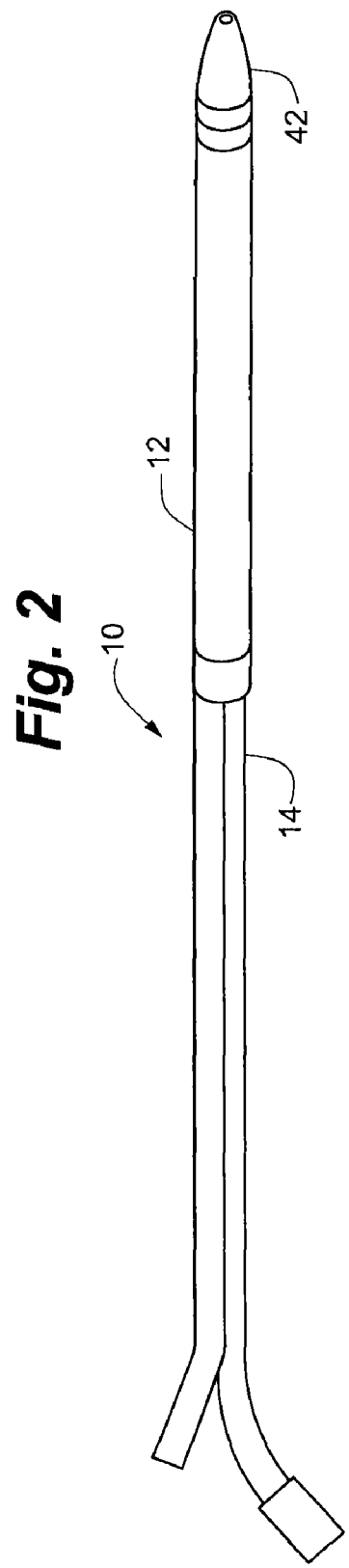
FIG. 2 is schematic depiction of the coaxial guide catheter and tapered inner catheter assembled in accordance with the present invention.
Figure 3:
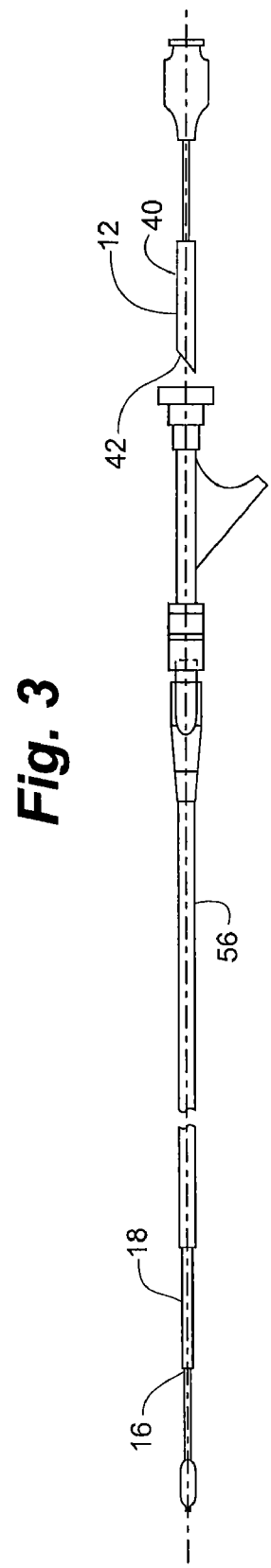
FIG. 3 is a plan view of a guide catheter, the coaxial guide catheter, and a treatment catheter in accordance with the present invention.
Figure 4:
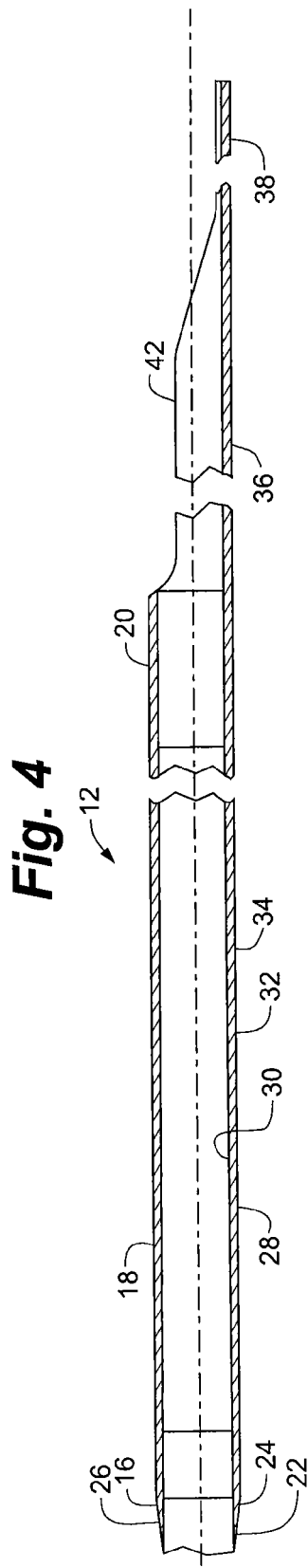
FIG. 4 is a sectional view of the coaxial guide catheter in accordance with the present invention.
Figure 5:
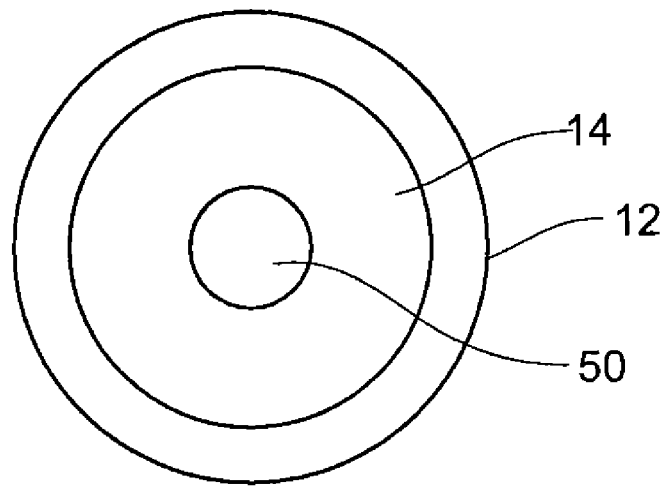
FIG. 5 is a cross sectional view of the coaxial guide catheter and tapered inner catheter in accordance with the present invention.
Figure 6:
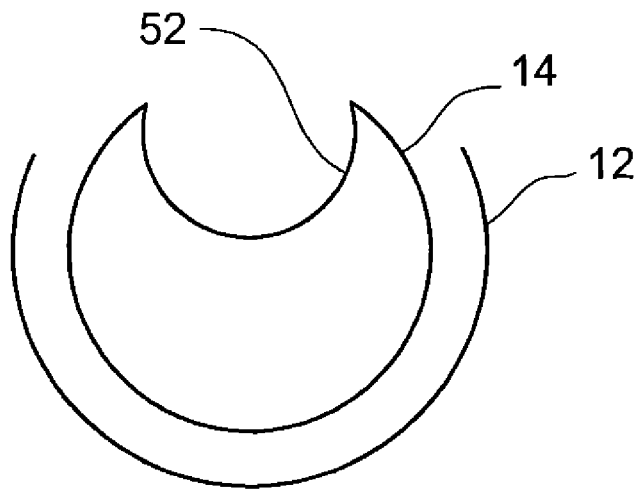
FIG. 6 is another cross sectional view of the coaxial guide catheter and tapered inner catheter in accordance with the present invention.

Referring to FIGS. 1 and 2, coaxial guide catheter assembly 10 of the present invention generally includes coaxial guide catheter 12 and tapered inner catheter 14.

Coaxial guide catheter 12 generally includes tip portion 16, reinforced portion 18, and rigid portion 20. The overall length of the coaxial guide catheter typically can be approximately 125 cm. This length should not be considered limiting.

Tip portion 16 generally includes bump tip 22 and marker band 24. Bump tip 22 includes taper 26. Bump tip 24 is relatively flexible and may be formed, for example, from 4033 Pebax®. Bump tip 22 may be yellow or another high visibility color for ease of handling.

Marker band 24 is formed of a radiopaque material such as platinum/iridium alloy usually at a 90/10 ratio. Marker band 24 may be sandwiched between an outer Pebax® material 28 and a PTFE liner 30. Outer Pebax® material 28 in this location may be formed of 5533 Pebax, for example.

Reinforced portion 18 includes braid or coil reinforcement 32. Braid or coil reinforcement 32 may be formed of metal, plastic, graphite, or composite structures known to the art. Reinforced portion 18 may be lined on the interior by PTFE liner 30 and covered on the exterior by Pebax® material 28. Tip portion 16 and reinforced portion 18 together form a substantially cylindrical structure. Braid or coil reinforcement 32 may extend approximately 20 to 30 cm. In one exemplary embodiment, braid or coiled portion has a length of approximately 32 to 36 cm.

Rigid portion 20 may be secured to braid or coil reinforcement by, for example, welding or bonding. Rigid portion 20 may be formed from a hypotube or a section of stainless steel or Nitinol tubing. Other substantially rigid materials may be used as well. Rigid portion 20 includes first full circumference portion 34, hemicylindrical portion 36, arcuate portion 38, and second full circumference portion 40.

First full circumference portion 34 is joined to braid or coil reinforcement 32. First full circumference portion 34 extends for a relatively short distance, for example, 0.25 cm.

Hemicylindrical portion 36 desirably includes 40% to 70% of the circumference of the tube. Hemicylindrical portion 36 may extend, for example, approximately 20 to 75 cm in length.

Hemicylindrical portion 36 tapers into arcuate portion 38.

Arcuate portion 38 extends from 25% to 40% of the circumference of the tube. Arcuate portion 38 may extend linearly, for example, for about 15 cm.

Arcuate portion 38 connects to second full circumference portion 40. Second full circumference portion 40 may extend for a short distance, for example, approximately 3 cm.

Tapered inner catheter 14 generally includes tapered inner catheter tip 42 and cutout portion 44. Tapered inner catheter tip 42 tapers gradually from the diameter of a guide wire to the diameter of tip portion 16.

Tapered inner catheter tip 42 includes tapered portion 46 at a distal end thereof, and straight portion 48. Both tapered portion 46 and straight portion 48 are pierced by lumen 50.

Cutout portion 44 defines a concave track 52 along its length. Concave track 52 is continuous with lumen 50.

Tapered inner catheter 14 may also include clip 54 at a proximal end thereof to releasably join tapered inner catheter 14 to coaxial guide catheter 12. Thus, tapered inner catheter 14 is keyed to coaxial guide catheter 12.

Coaxial guide catheter 12 may include, starting at its distal end, a first portion having a flexural modulus of about 13,000 PSI plus or minus 5000 PSI, a second portion having a flexural modulus of about 29,000 PSI plus or minus 10,000 PSI, a third portion having a flexural modulus of about 49,000 PSI plus or minus 10,000 PSI and a fourth portion having a flexural modulus of about 107,000 PSI plus or minus 20,000 PSI. Coaxial guide catheter 12 may be formed, for example, of 4033 Pebax® at bump tip 22 for the first 0.1 cm. This portion may followed by a section about three cm long of 5533 Pebax® that covers marker band 24 and the distal portion of braid or coil reinforcement 32. Next may come an approximately five cm portion of 6333 Pebax® which encloses part of braid or coil reinforcement 32 followed by an approximately twenty seven cm portion of 7233 Pebax® covering the most proximal portion of braid or coil reinforcement 32. Braid or coil reinforcement 32 is bonded to rigid portion 20 which may be formed from stainless steel or a similar biocompatible material. Rigid portion 20 may extend for approximately ninety cm and include first full circumference portion 34 (approximately 0.25 cm), hemicylindrical portion 36 (approximately seventy five cm), arcuate portion (approximately fifteen cm) and second full circumference portion (approximately three cm.) Rigid portion 20 may be formed from a stainless steel or Nitinol hypo tube.

Figure 7:
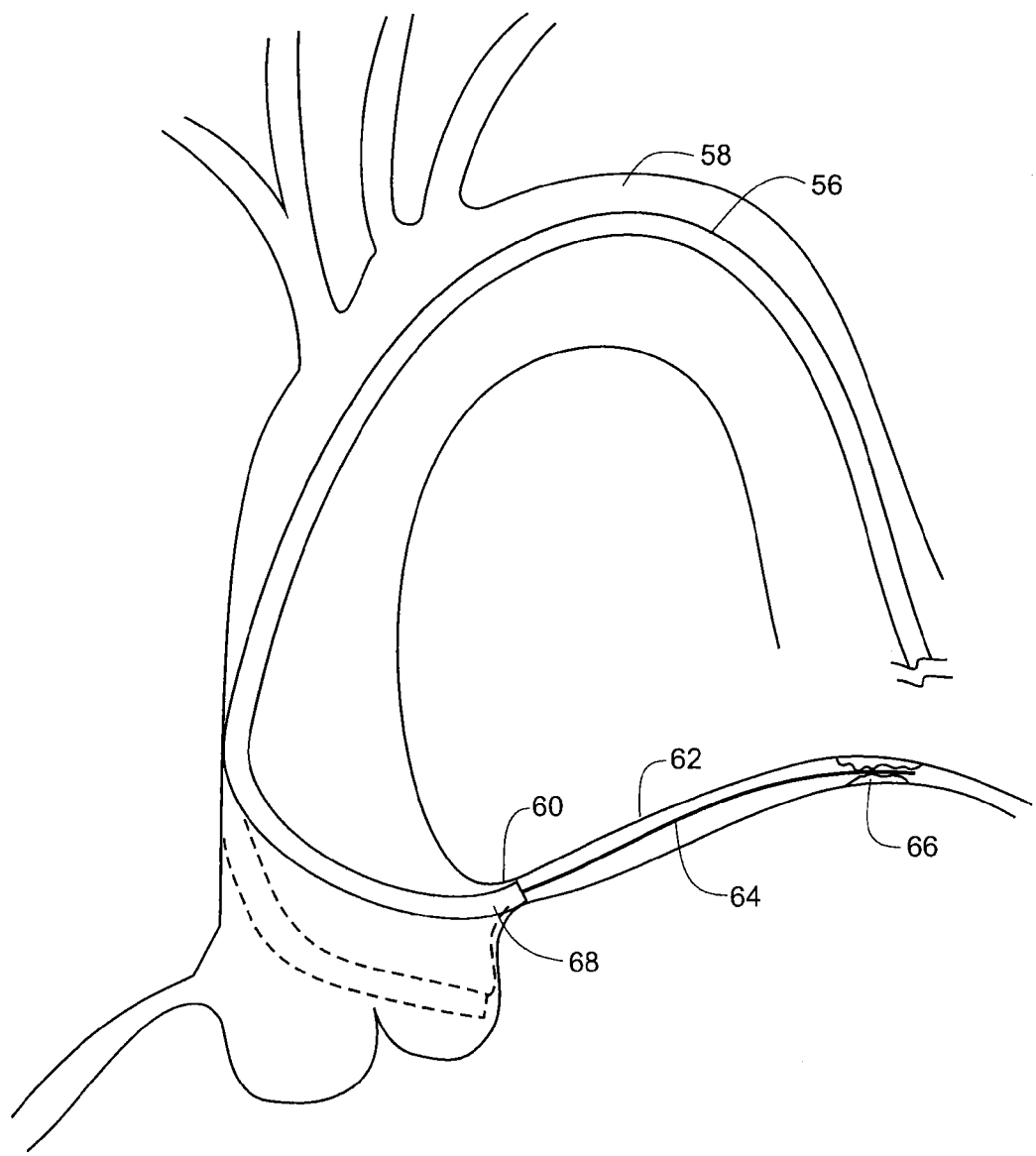
FIG. 7 is a schematic view of a guide catheter and a guidewire located in an aortic arch and a coronary artery and the guide catheter and guidewire in a second position depicted in phantom.

FIG. 7 depicts a typical guide catheter 56 passing through aortic arch 58 into ostium 60 of coronary artery 62. FIG. 7 also depicts guidewire 64 passing through the guide catheter 56 and into coronary artery 62. Located in coronary artery 62 is stenotic lesion 66. In a typical procedure, guidewire 64 is placed through the aortic arch 58 and into the ostium 60 of the coronary artery. 62. The guide catheter 56 is passed over guidewire 64 until distal end 68 of guide catheter 56 is seated in ostium 60 of coronary artery 62. Force is then applied to the guidewire 64 to push guidewire 64 past stenotic lesion 66 or an occlusive lesion (not shown). Once the guidewire 64 is pushed past stenotic lesion 66 or occlusive lesion (not shown), a treating catheter including a stent or balloon can be passed along the guidewire to stenotic lesion 66 or occlusive lesion (not shown). The lesion can then be treated.

As can be seen in phantom, in FIG. 7, the application of force to guidewire 64 can cause guide catheter 56 to dislodge from ostium 60 of coronary artery 62. This can occur in the case of a tough stenotic lesion 66 or occlusive lesion (not shown) when it is difficult to pass the guidewire 64 beyond the stenotic lesion 66 or occlusive lesion (not shown).

Figure 8:
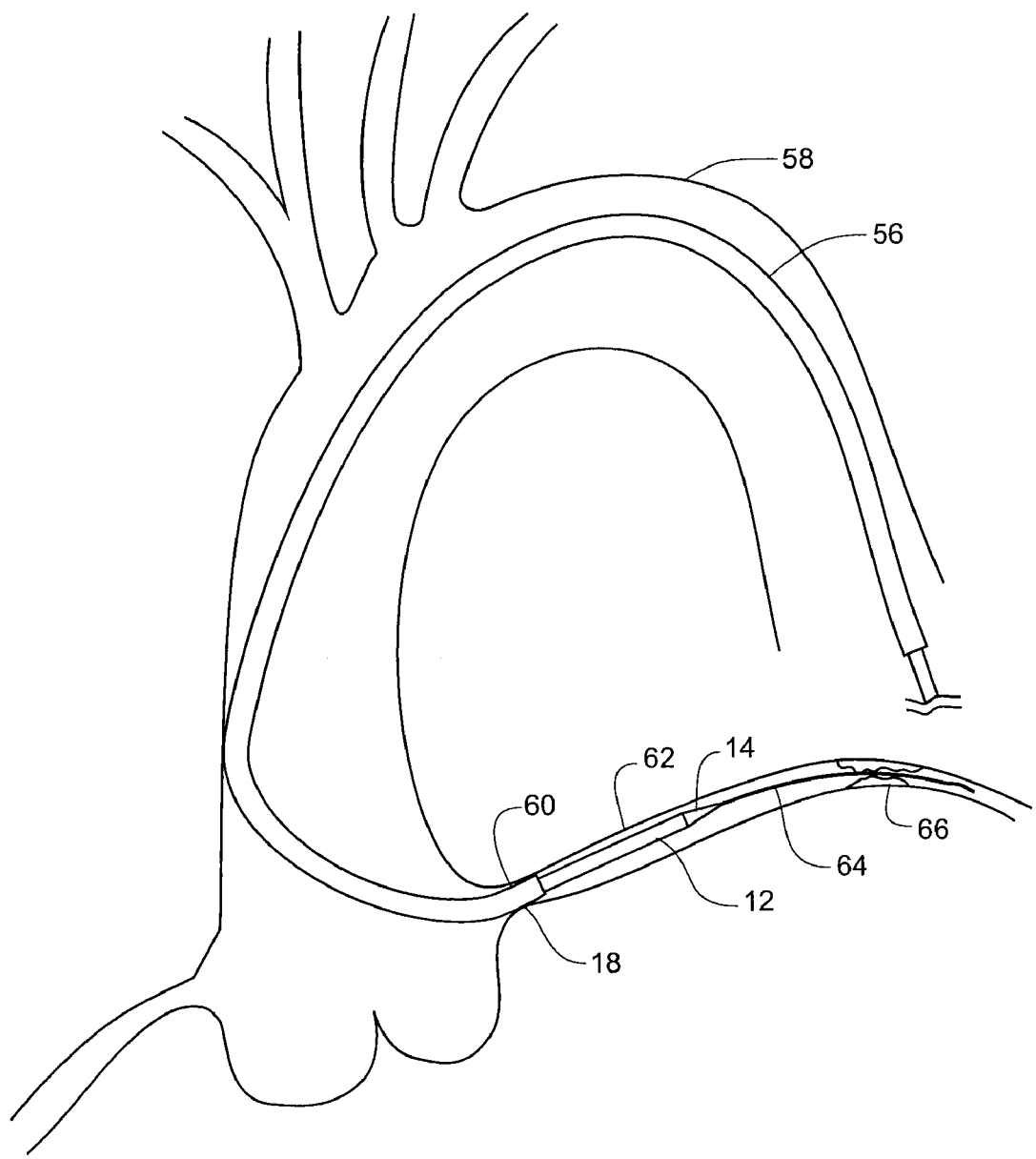
FIG. 8 is a schematic view of a guide catheter, a guidewire, a coaxial guide catheter in accordance with the present invention and a tapered inner catheter located in the aortic arch and coronary artery.

Referring the FIG. 8 coaxial guide catheter 12 is depicted as used with guide catheter 56, guidewire 64, and tapered inner catheter 14. Here, coaxial guide catheter 12 with tapered inner catheter 14 is passed through guide catheter 56 and over guidewire 64 into coronary artery 62 after the guide catheter 56 has been placed in the ostium 60 of coronary artery 62, as depicted in FIG. 7. Coaxial guide catheter 12, with tapered inner catheter 14, provides an inner support member for proper translation over guidewire 64. Tapered inner catheter tip 42 provides a distal tapered transition from guidewire 64 to coaxial guide catheter 12. Once coaxial guide catheter 12 is in place, tapered inner catheter 14 is removed from the inside of coaxial guide catheter 12.

Figure 9:
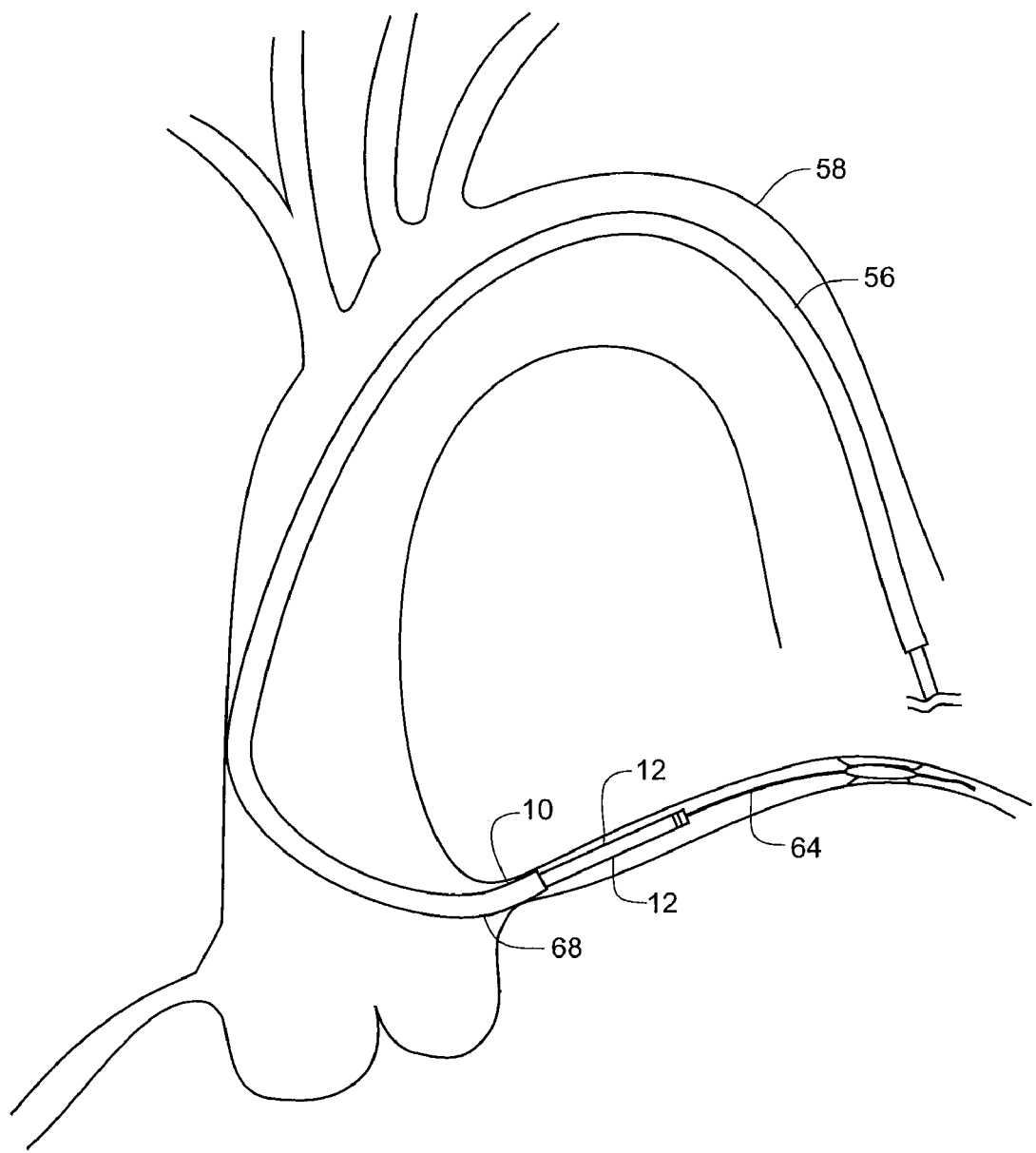
FIG. 9 is a schematic view of a guide catheter, a guidewire and a coaxial guide catheter in accordance with the present invention located in the aortic arch and coronary artery.

Coaxial guide catheter 12 is now ready to accept a treatment catheter such as a stent or balloon catheter. Referring to FIG. 9, the combination of guide catheter 56 with coaxial guide catheter 12 inserted into ostium 60 of coronary artery 62 provides improved distal anchoring of guide catheter 56 and coaxial guide catheter 12. The presence of coaxial guide catheter 12 within guide catheter 56 also provides stiffer back up support than guide catheter 56 alone. The combination of improved distal anchoring and stiffening of the guide catheter 56/coaxial guide catheter 12 combination provides additional back up support to resist dislodging of guide catheter 56 from ostium 60 when force is applied to guidewire 64 to pass through stenotic lesion 66 or another lesion. In addition, the improved back up support assists in the positioning of a treating catheter that may include a stent or balloon.

Referring to FIGS. 10 and 11, in some embodiments of coaxial guide catheter 12, rigid portion 20 may be perforated by relief cuts 70. Relief cuts 70 may be classed into first group 72 and second group 74.

First group 72 may be located near to the juncture between rigid portion 20 and reinforced portion 18. First group 72 of relief cuts 70, are relatively closely spaced. For example, first group 72 of relief cuts 70 may be spaced approximately 0.010 inches apart. First group 72 of relief cuts 70 extends for a relatively short distance, for example, approximately 2 inches.

Second group 74 of relief cuts 70 may extend for a relatively long distance, for example, approximately 30-35 inches. Second group 74 of relief cuts 70 are spaced farther apart than first group 72. For example, relief cuts 70 of second group 74 may be spaced approximately 0.020 inches between cuts. Referring particularly to FIG. 11, relief cuts 70 may include single cuts 76 and double cuts 78. Single cuts 76 may include an individual linear cut, as can be seen in FIG. 11. Double cuts 78 may include two linear cuts along a single line but separated by a short section of uncut structure. Typically, single cuts 76 and double cuts 78 are alternated along the length of rigid portion 20. Generally, the overall length of single cut 76 may be less than the overall length of two double cuts 78.

In an embodiment depicted in FIGS. 12-15, rigid portion includes full circumference portion 80, greater than 180° portion 82, and less than 180° portion 84. Greater than 180° portion 82 may, for example, include structure forming approximately 300° of the circumference of the cylinder. Less than 180° portion may include, for example, structure forming approximately 90° of the circumference of a cylinder. Greater than 180° portion 82 may extend approximately 22-25 inches. Greater than 180° portion 82 holds tapered inner catheter 14 within rigid portion 20.

When tapered inner catheter is inserted into coaxial guide catheter 12 greater than 180°, portion 82 grips tapered inner catheter 14 which is exposed through the opening in greater than 180° portion 82. Thus, the overall structure of tapered inner catheter 14 along with greater than 180° portion 82 is substantially cylindrical. Accordingly, when inserted through a guide catheter 56 having a Touhey-Borst style adapter, the Touhey-Borst style adapter can still seal around rigid portion 20 and enclosed inner tapered catheter 14.

Referring to FIG. 16, another embodiment of coaxial guide catheter assembly 10 includes coaxial guide catheter 12 and tapered inner catheter 14. Tapered inner catheter 14 is keyed to coaxial guide catheter 12 at hub 86.

Figure 17:
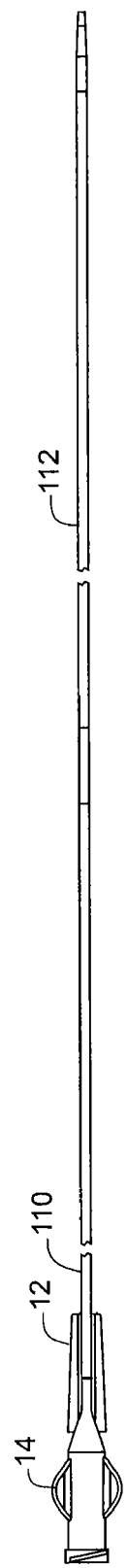
FIG. 17 is a plan view of a coaxial guide catheter having a longer rail segment and a tapered inner catheter in accordance with the present invention.
Figure 18:
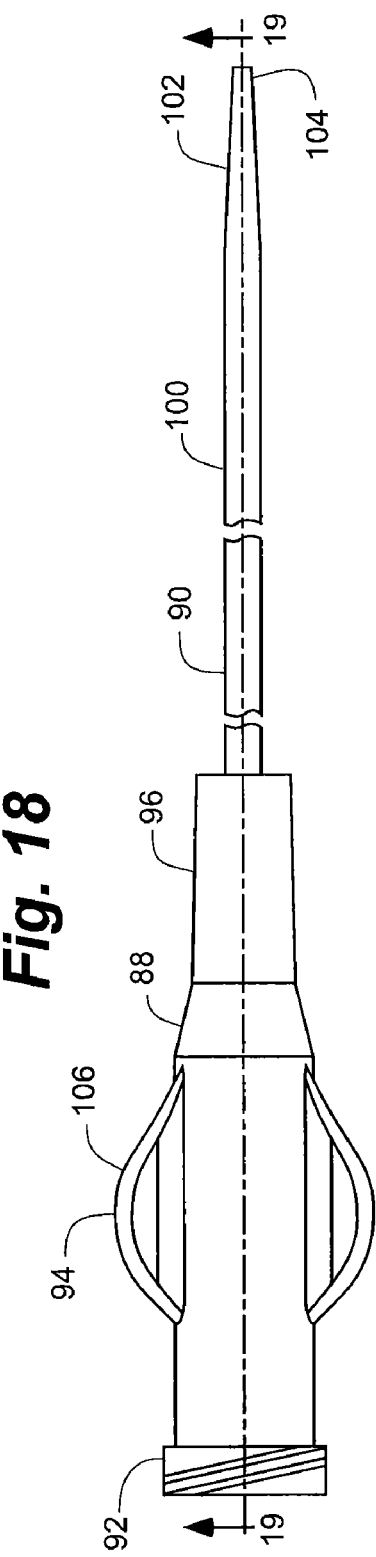
FIG. 18 is a plan view of the tapered inner catheter as depicted in the FIG. 17.

Referring to FIGS. 17 and 18, tapered inner catheter 14 generally includes connector hub 88 and catheter tube 90.

Connector hub 88 generally includes connector portion 92, grip portion 94 and joining portion 96. Connector hub 88 defines funnel portion 98 therein.

Catheter tube 90 generally includes straight portion 100, tapered portion 102 and marker band tip 104. Catheter tube 90 is joined to connector hub 88 at joining portion 96. Tapered inner catheter 14 may be formed in whole or in part from low-density polyethylene plastic, for example. Other suitable materials known to the catheter arts may be used as well.

Grip portion 94 desirably includes gripping ears 106. Gripping ears 106 may extend outwardly from grip portion 94 substantially radially and be shaped for convenient gripping by a physician.

Figure 19:
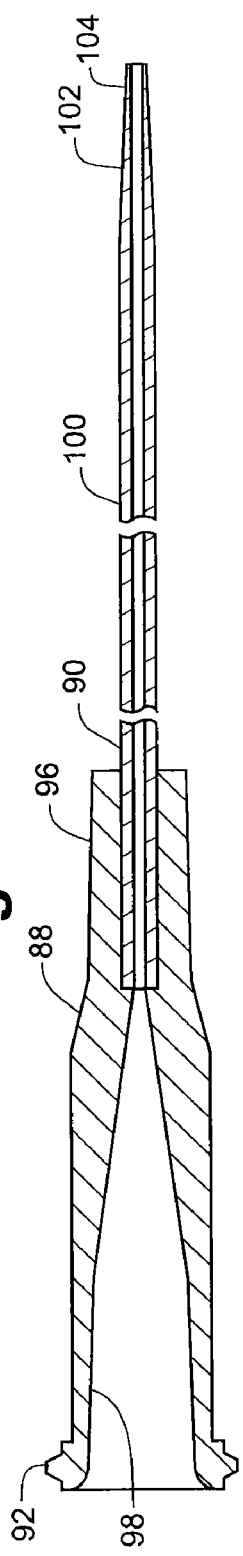
FIG. 19 is a cross-sectional view of the tapered inner catheter taken along section lines 19-19 of FIG. 18.

Referring to FIGS. 19 through 21, in this embodiment, coaxial guide catheter 12 includes interrupted hub 108, hemi-tube portion 110, braided portion 112 and tip portion 114.

Interrupted hub 108 defines an opening 116, along a side thereof. Interrupted hub 108 may be substantially C-shaped or U-shaped in cross section. Opening 116 is sized so that tapered inner catheter 14 may be passed readily therethrough in a direction perpendicular to the long axes of both interrupted hub 108 and tapered inner catheter 14. Hemi-tube portion 110 is immediately distal to interrupted hub 108. Hemi-tube portion 110 may be formed, for example, from a metal hypo tube forming approximately 50% of the circumference of a cylinder. Hemi-tube portion 110 is aligned so that opening 116 of interrupted hub 108 is coextensive with opening 118 of hemi-tube portion 110. Hemi-tube portion 110 is joined to braided portion 112, for example, by adhesive, bonding or welding. The location where hemi-tube portion 110 and braided portion 112 join defines the entire circumference of a cylinder.

Braided portion 112 may be reinforced by a coil or braid, 120. Coil or braid 120 may be formed of metal or another suitable reinforcing material.

Tip portion 114 is generally not reinforced and is substantially soft. Tip portion 114 is similarly structured to tapered inner catheter tip 42. Tip portion 114 may include a radiopaque marker band 24.

Beginning at the distal end of coaxial guide catheter 12, tip portion 114 may be formed substantially of, for example, 2533 Pebax® This may be followed by a section of 3533 Pebax®, then by a section of 5533 Pebax®, then by a further section of 7233 Pebax®. These Pebax® portions may all incorporate, for example, about 20% barium sulfate ($BaSO_4$).

In one embodiment, tip portion 114 and braided portion 112 may have an overall length together of approximately one hundred nine centimeters. Hemi-tube portion 110 and interrupted hub 108 may together have an overall length of approximately eighteen centimeters.

In this embodiment, coaxial guide catheter 12 may be lined with a PTFE liner 122.

In operation, a guide catheter 56 is inserted into a major blood vessel in the body such as aortic arch 58 over guidewire 64 and the distal end 68 of guide catheter 56 is brought into proximity of ostium 60 of a smaller branch blood vessel, such as coronary artery 62, that it is desired to enter. Coaxial guide catheter 12, with tapered inner catheter 14, is inserted through guide catheter 56 and over guidewire 64. Guide catheter 56, guidewire 64, coaxial guide catheter 12, and tapered inner catheter 14 are manipulated to insert tapered inner catheter tip 42 into the ostium 60 of the blood vessel that branches off from the major blood vessel. The bump tip 22 of coaxial guide catheter 12 is inserted with tapered inner catheter tip 42 well into ostium 60 of coronary artery 62 or other blood vessel until bump tip 22 of coaxial guide catheter 12 achieves a deep seated position. Tapered inner catheter 14 is then withdrawn from the lumen of coaxial guide catheter 12. An interventional cardiology treatment device such as a catheter bearing a stent or a balloon (not shown) is then inserted through the lumen of coaxial guide catheter 12 which remains inside guide catheter 56.

When the interventional cardiology device reaches a stenosis or blockage in coronary artery 62 or another branch blood vessel, force may be applied to the interventional cardiology device catheter while reinforced portion 18 and rigid portion 20 of coaxial guide catheter 12 provide back up support. The back force that would tend to dislodge bump tip 22 from a deep seated position in the ostium in the branch blood vessel is transferred through reinforced portion 18 to rigid portion 20 of coaxial guide catheter 12. A physician may apply a force to the proximal end of the coaxial guide catheter 12 to resist dislodging of bump tip 22 from the ostium of the branch artery.

One advantage of the present invention over prior art approaches is that the present invention does not interfere with the injection of fluids via the Y-adapter of guide catheter 56 as does the use of a smaller catheter within a larger catheter.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A system for use with interventional cardiology devices adapted to be insertable into a branch artery, the system comprising:

a guide catheter having a continuous lumen extending for a predefined length from a proximal end at a hemostatic valve to a distal end adapted to be placed in the branch artery, the continuous lumen of the guide catheter having a circular cross-sectional inner diameter sized such that interventional cardiology devices are insertable into and through the continuous lumen of the guide catheter; and a device adapted for use with the guide catheter, including:
structure and having a circular cross-section and a length that is shorter than the predefined length of the continuous lumen of the guide catheter, the tubular structure having a cross-sectional outer diameter sized to be insertable through the cross-sectional inner diameter of the continuous lumen of the guide catheter and defining a coaxial lumen having a cross-sectional inner diameter through which interventional cardiology devices are insertable; and a substantially rigid portion proximal of and operably connected to, and more rigid along a longitudinal axis rain a structure without a lumen having a maximal cross-sectional dimension at a proximal portion that is smaller than the cross-sectional outer diameter of the flexible tip portion and having a length that, when combined with the length of the flexible distal tip portion, defines a total length of the device along the longitudinal axis that is longer than the length of the continuous lumen of the guide catheter, such that when at least a distal portion of the flexible tip portion is extended distally of the distal end of the guide catheter, at least a portion of the proximal portion of the substantially rigid portion extends proximally through the hemostatic valve in common with interventional cardiology devices that are insertable into the guide catheter.

2. The system of claim 1, wherein the tubular structure includes a distal portion adapted to be extended beyond the distal end of the guide catheter while a proximal portion remains within the lumen of the guide catheter, such that the device assists in resisting axial and shear forces exerted by the interventional cardiology device passed through and beyond the coaxial lumen that would otherwise tend to dislodge the guide catheter from the branch artery.

3. The system of claim 2, wherein the proximal portion of the tubular structure further comprises structure defining a proximal side opening extending for a distance along the longitudinal axis, and accessible from a longitudinal side defined transverse to the longitudinal axis, to receive the interventional cardiology devices into the coaxial lumen while the proximal portion remains within the lumen of the guide catheter.

4. The system of claim 3, wherein the proximal side opening includes structure defining a full circumference portion and structure defining a partially cylindrical portion.

5. The system of claim 1, wherein the tubular structure includes a flexible cylindrical distal tip portion and a flexible cylindrical reinforced portion proximal to the flexible distal tip portion.

6. The system of claim 5, wherein the flexible cylindrical reinforced portion is reinforced with metallic elements in a braided or coiled pattern.

7. The system of claim 2, wherein the flexible cylindrical distal tip portion further comprises a radiopaque marker proximate a distal tip.

8. The system of claim 1, wherein the cross-sectional inner diameter of the coaxial lumen of the tubular structure is not more than one French smaller than the cross-sectional inner diameter of the guide catheter.

9. The system of claim 1, wherein the substantially rigid portion includes from distal to proximal direction, a cross-sectional shape having a full circumference portion, a hemicylindrical portion and an arcuate portion.

10. The system of claim 1, wherein the predefined length of the guide catheter is about 100 cm and the total length of the device is about 125 cm.

11. The system of claim 1, further comprising a kit that includes the guide catheter and the device in a common sterile package.

12. A system for use with interventional cardiology devices adapted to be insertable into a branch artery, the system comprising:
 a guide catheter having a continuous lumen extending for a predefined length from a proximal end at a hemostatic valve to a distal end adapted to be placed in the branch artery, the continuous lumen of the guide catheter having a circular cross-section and a cross-sectional inner diameter sized such that interventional cardiology devices are insertable into and through the continuous lumen of the guide catheter; and
 a device adapted for use with the guide catheter, including:
  an elongate structure having an overall length that is longer than the predefined length of the continuous lumen of the guide catheter, the elongate structure including:
   structure and having a circular cross-section that is smaller than the circular cross-section of the continuous lumen of the guide catheter and a length that is shorter than the predefined length of the continuous lumen of the guide catheter, the flexible tip portion having a cross-sectional outer diameter sized to be insertable through the cross-sectional inner diameter of the continuous lumen of the guide catheter and defining a coaxial lumen having a cross-sectional inner diameter through which interventional cardiology devices are insertable;
   a reinforced portion proximal to the flexible tip portion; and
   a substantially rigid portion proximal of, connected to, and more rigid along a longitudinal axis rail structure without a lumen having a maximal cross-sectional dimension at a proximal portion that is smaller than the cross-sectional outer diameter of the flexible tip portion, such that when at least a distal portion of the flexible tip portion is extended distally of the distal end of the guide catheter with at least proximal portion of the reinforced portion remaining within the continuous lumen of the guide catheter, at least a portion of the proximal portion of the substantially rigid portion extends proximally through the hemostatic valve in common with interventional cardiology devices that are insertable into the guide catheter.

13. The system of claim 12, wherein, when the distal portion of the flexible tip portion is insertable through the continuous lumen of the guide catheter and beyond the distal end of the guide catheter, the device assists in resisting axial and shear forces exerted by an interventional cardiology device passed through and beyond the coaxial lumen that would otherwise tend to dislodge the guide catheter from the branch artery.

14. The system of claim 12, wherein the substantially rigid portion further includes a partially cylindrical portion defining an opening extending for a distance along a side thereof defined transverse to a longitudinal axis that is adapted to receive an interventional cardiology device passed through continuous lumen of the guide catheter and into the coaxial lumen while the device is inserted into the continuous lumen, the opening extending substantially along at least a portion of a length of the substantially rigid portion.

15. The system of claim 12, wherein, after the device is inserted into the continuous lumen of the guide catheter, the device presents an overall effective length of a coaxial lumen through which an interventional cardiology device may be inserted while utilizing only a single hemostatic valve and without any telescoping structure preassembled prior to the device being inserted into the continuous lumen of the guide catheter.

16. The system of claim 12, the device further comprising a radiopaque marker proximate the distal portion of the flexible tip portion.

17. The system of claim 12, wherein the reinforced portion of the device is reinforced with metallic elements in a braided or coiled pattern.

18. The system of claim 12, wherein the cross-sectional inner diameter of the coaxial lumen of the flexible distal portion is not more than one French smaller than the cross-sectional inner diameter of the guide catheter.

19. The system of claim 12, wherein the substantially rigid portion includes, from distal to proximal, a cross-sectional shape having a full circumference portion, a hemicylindrical portion and an arcuate portion.

20. The system of claim 12, wherein the elongate structure includes, starting at the distal portion of the flexible distal portion, at least a first portion having a first flexural modulus, a second portion having a second flexural modulus greater than the first flexural modulus, and a third portion having a third flexural modulus greater than the second flexural modulus.

21. The system of claim 20, in which the first flexural modulus is about 13,000 PSI plus or minus 5000 PSI, the second flexural modulus is about 29,000 PSI plus or minus 10,000 PSI, and the third portion flexural modulus is about 49,000 PSI plus or minus 10,000 PSI.

22. The system of claim 20, in which the first portion is about 0.1 cm in length, the second portion is about three cm in length, and the third portion is about five cm in length.

23. The system of claim 12, wherein the predefined length of the guide catheter is about 100 cm and the total length of the device is about 125 cm.

24. The system of claim 12, further comprising a kit that includes the guide catheter and the device in a common sterile package.

* * * * *

UNITED STATES PATENT AND TRADEMARK OFFICE
CERTIFICATE OF CORRECTION

| | | |
|---|---|---|
| PATENT NO. | : 8,292,850 B2 | Page 1 of 1 |
| APPLICATION NO. | : 13/359059 | |
| DATED | : October 23, 2012 | |
| INVENTOR(S) | : Howard Root et al. | |

It is certified that error appears in the above-identified patent and that said Letters Patent is hereby corrected as shown below:

In Column 10, claim 1, line 46, prior to "structure", insert
-- a flexible tip portion defining a tubular --

In Column 10, claim 1, line 57, delete "rain a" and insert -- than the flexible tip portion and defining a rail" --

In Column 11, claim 12, line 64, prior to "structure", insert
-- a flexible tip portion defining a tubular --

In Column 12, claim 12, lines 11-12, prior to "structure", insert
-- than the flexible tip portion and defining a --

Signed and Sealed this
Twenty-second Day of January, 2013

David J. Kappos
*Director of the United States Patent and Trademark Office*